(12) United States Patent
Bornzin et al.

(10) Patent No.: US 6,658,283 B1
(45) Date of Patent: Dec. 2, 2003

(54) IMPLANTABLE CARDIAC STIMULATION DEVICE, SYSTEM AND METHOD WHICH PROVIDES AN ELECTROGRAM SIGNAL HAVING THE APPEARANCE OF A SURFACE ELECTROCARDIOGRAM

(75) Inventors: Gene A. Bornzin, Simi Valley, CA (US); Joseph J. Florio, La Canada, CA (US); Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 119 days.

(21) Appl. No.: 09/963,207

(22) Filed: Sep. 25, 2001

(51) Int. Cl.$^7$ .............................................. A61B 5/0402
(52) U.S. Cl. ...................................................... 600/510
(58) Field of Search .................. 607/1–28; 600/508–521

(56) References Cited

U.S. PATENT DOCUMENTS

| | | | |
|---|---|---|---|
| 5,324,310 A | 6/1994 | Greeninger et al. .......... | 607/28 |
| 5,448,997 A | * 9/1995 | Kruse et al. | |
| 5,466,254 A | 11/1995 | Helland ....................... | 607/123 |
| 5,542,430 A | * 8/1996 | Farrugia et al. | |
| 5,605,158 A | 2/1997 | Snell ........................... | 128/696 |
| 5,740,811 A | 4/1998 | Hedberg et al. ............. | 128/697 |
| 5,954,666 A | 9/1999 | Snell ........................... | 600/523 |
| 6,249,705 B1 | 6/2001 | Snell ........................... | 607/59 |
| 2002/0123770 A1 | 9/2002 | Combs et al. ................. | 607/9 |

OTHER PUBLICATIONS

Medtronic Reveal® Plus Insertable Loop Recorder Brochure; pp 1–10; publication date unknown.
Medtronic Reveal® Plus Insertable Loop Recorder Implant & Programming Guide; pp 1–35 publication date unknown.

* cited by examiner

*Primary Examiner*—Scott M. Getzow

(57) ABSTRACT

An implantable cardiac stimulation system and method provides an external display of a heart activity signal sensed internally by an implantable cardiac stimulation device which has the appearance of a surface EKG. The heart activity signal is sensed by the implanted device and is processed by the device or the external display to have frequency characteristics resembling that of a surface EKG. The heart activity signal to be displayed takes the form of an intracardiac electrogram signal with a low frequency roll-on of no greater than 0.4 Hz and a high frequency cutoff of no less than 20 Hz. This provides a heart activity signal for display which has the appearance and most attributes of a surface EKG.

43 Claims, 5 Drawing Sheets

FIG. 4

| SEL 0 | SEL 1 | SEL 2 | ATRIAL ELECTRODE CONFIGURATION |
|---|---|---|---|
| 0 | 0 | 0 | $A_R$ TIP TO $V_R$ RING |
| 0 | 0 | 1 | $A_R$ TIP TO CASE |
| 0 | 1 | 0 | $A_R$ TIP TO $V_R$ RING |
| 0 | 1 | 1 | $A_R$ TIP TO $A_R$ RING |
| 1 | 0 | 0 | $A_R$ RING TO $V_R$ RING |
| 1 | 0 | 1 | $A_R$ RING TO CASE |
| 1 | 1 | 0 | $A_R$ RING TO $V_R$ TIP |
| 1 | 1 | 1 | $A_R$ RING TO $A_R$ RING |

FIG. 5

| SEL 0 | SEL 1 | SEL 2 | |
|---|---|---|---|
| 0 | 0 | 0 | $V_R$ TIP TO $A_R$ RING |
| 0 | 0 | 1 | $V_R$ TIP TO CASE |
| 0 | 1 | 0 | $V_R$ TIP TO $A_R$ RING |
| 0 | 1 | 1 | $V_R$ TIP TO $V_R$ RING |
| 1 | 0 | 0 | $V_R$ RING TO $A_R$ RING |
| 1 | 0 | 1 | $V_R$ RING TO CASE |
| 1 | 1 | 0 | $V_R$ RING TO $A_R$ TIP |
| 1 | 1 | 1 | $V_R$ RING TO $V_R$ RING |

IMPLANTABLE CARDIAC STIMULATION DEVICE, SYSTEM AND METHOD WHICH PROVIDES AN ELECTROGRAM SIGNAL HAVING THE APPEARANCE OF A SURFACE ELECTROCARDIOGRAM

FIELD OF THE INVENTION

The present invention generally relates to an implantable cardiac device. The present invention more particularly relates to an implantable cardiac stimulation device and external display for displaying an electrogram which resembles a surface electrocardiogram.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as having two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves)and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Implantable cardiac stimulation devices conventionally include an internal telemetry circuit permitting the devices to communicate with an external programmer. The external programmers also include a telemetry circuit with an external antenna or "wand" which is held over the implant site to allow the communication between the programmer and the implanted device. With the communication channel thus established, the programmer permits the attending medical personnel to set device operating modes and stimulation and sensing parameters within the device. The communication channel also permits the device to convey to the external programmer operating and sensed physiological data for display. The physiological data may include an intracardiac electrogram (IEGM). The IEGM may be prestored in the device and conveyed to the programmer responsive to a suitable external command from the programmer. The IEGMs are typically stored in response to high rate ventricular events or high rate atrial event triggers. The result is that physicians have more insight into the operation of the devices and have more information about the underlying rhythm that interacts with the device.

In addition to the IEGMs, physicians would like to be provided with a surface electrocardiogram (EKG). Their desire is based upon their day-to-day use of surface EKGs to make diagnosis of arrhythmias. Hence, with both IEGMs and surface EKGs, physicians will have more confidence that they will be able to discern exactly the underlying arrhythmic event that triggered the IEGM storage.

Unfortunately, implantable devices cannot provide surface EKGs. While some programmers of implantable cardiac stimulation systems do accommodate the display of surface EKGs, the surface EKGs available are taken at regular follow-up visits and thus after the arrhythmic event and IEGM storage have occurred. An after the fact surface EKG is not very helpful in support of a diagnosis of a prior arrhythmic episode.

The present invention represents a significant advancement in the provision of heart activity information to support a diagnosis of a prior arrhythmic event. More particularly, the present invention satisfies the need for both IEGMs and surface EKGs taken at the time of an arrhythmic event.

SUMMARY OF THE INVENTION

In accordance with broader aspects of the present invention, an implantable cardiac stimulation system and method provides an external display of a heart activity signal sensed internally by an implantable cardiac stimulation device which has the appearance of a surface EKG. The heart activity signal sensed by the implanted device is processed by the device or by the external display or programmer to have frequency characteristics resembling that of surface EKGs.

The system includes at least one implantable electrode that senses the cardiac electrical activity to provide an intracardiac electrogram signal. The intracardiac electrogram signal is high pass filtered with a low frequency cutoff or roll-on of no greater than 0.4 Hz and a high frequency cutoff of no less than 20 Hz. This provides a heart activity signal for display which has the appearance and most attributes of a surface EKG.

The filtering of the IEGM signal may be accomplished within the implanted device or within the external display or programmer. When the filter is provided within the implanted device, the filtered IEGM resembling a surface EKG may be stored within the device for later conveyance to the programmer or conveyed to the programmer in real time for display. When the filter is provided in the external programmer, the IEGM signal to be filtered for display may be the standard IEGM signal provided by the device.

The filter may be implemented in discrete component form or in the form of a digital filter. The digital filter may be an equalizer which enhances low frequency response of the IEGM.

Selective electrode configurations may be provided by the implanted system for providing the IEGM to be processed. The selectable electrode configurations preferably include unipolar atrial, unipolar ventricular or transchamber configurations. The electrode configurations may more specifically include atrial ring and ventricular ring electrodes, atrial tip and ventricular tip electrodes, and ventricular defibrillation electrodes.

BRIEF DESCRIPTION OF THE DRAWINGS

Further features and advantages of the present invention may be more readily understood by reference to the following description taken in conjunction with the accompanying drawings, in which:

FIG. 4 is a chart illustrating the manner in which a first sensing IEGM electrode configuration may be selected from a plurality of possible sensing electrode configurations;

FIG. 5 is a chart illustrating the manner in which a second sensing IEGM electrode configuration may be selected from a second plurality of possible sensing electrode configurations;

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
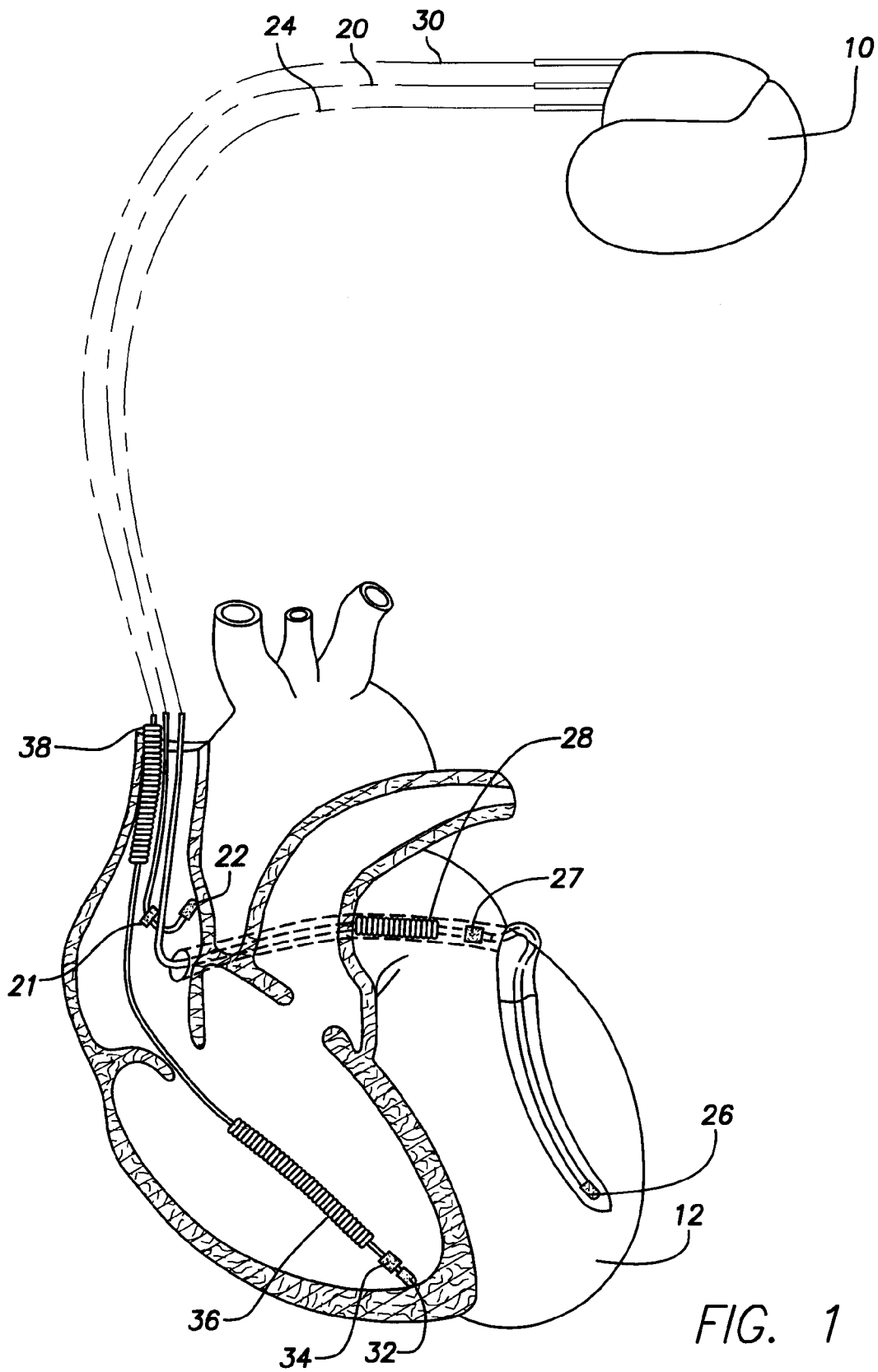
FIG. 1 is a simplified diagram illustrating an implantable stimulation device and lead system embodying the present invention for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may further include a right atrial ring electrode 21 to permit unipolar sensing with that electrode or bipolar sensing with the right atrial tip electrode 22.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
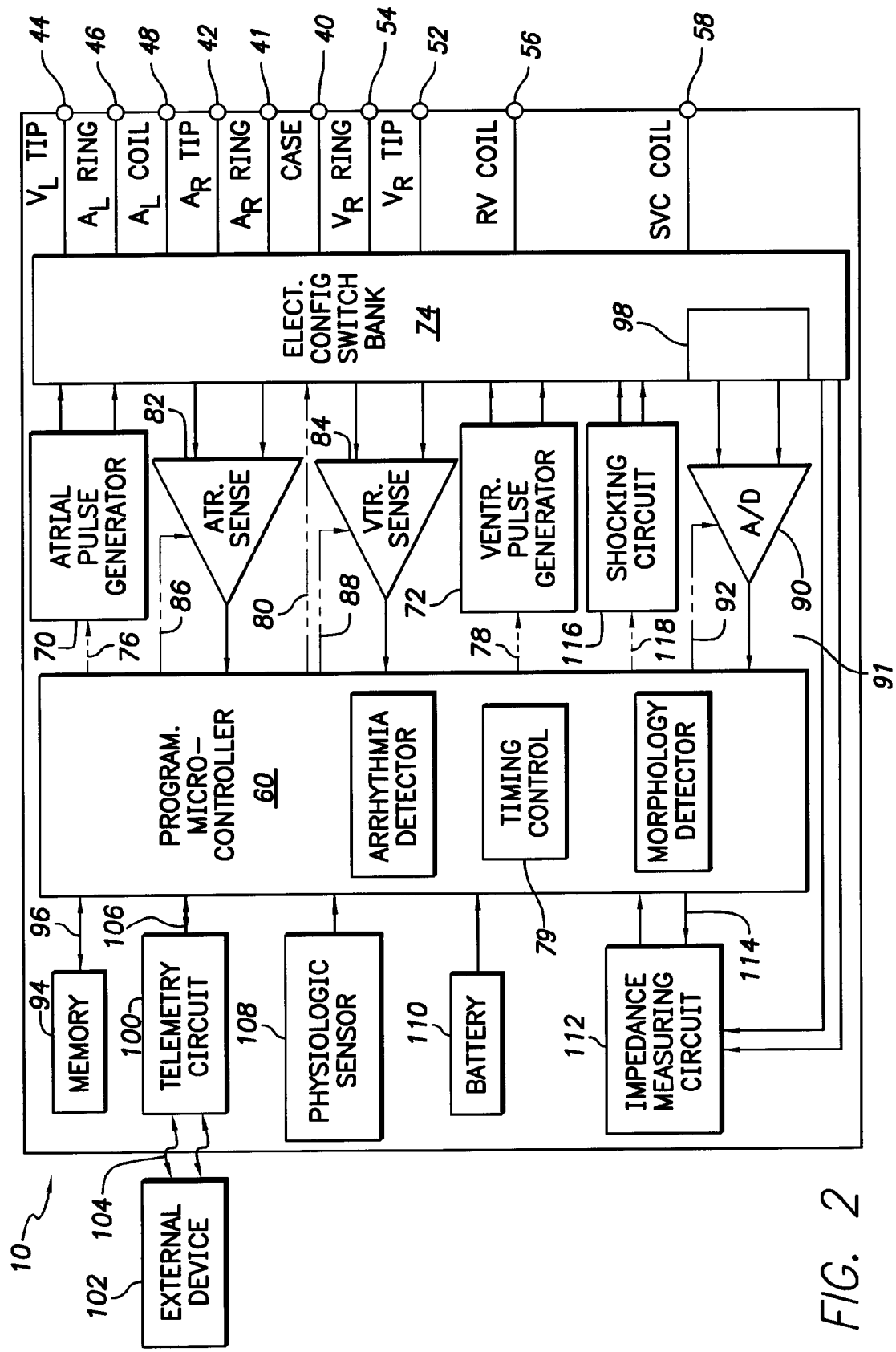
FIG. 2 is a functional block diagram of a multi-chamber implantable stimulation device embodying the present invention illustrating the basic elements of a stimulation device which can provide cardioversion, defibrillation and pacing stimulation in four chambers of the heart as well as a processed IEGM signal or an IEGM signal to be processed for providing a heart activity signal resembling a surface IEKG in accordance with the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring terminal ($A_R$ RING) 41 adapted for connection to the atrial ring electrode 21.

To achieve left chamber sensing, pacing and shocking, the connector includes at least a left ventricular tip terminal ($V_L$ TIP) 44, a left atrial ring terminal ($A_L$ RING) 46, and a left atrial shocking terminal (A_L COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (V_R TIP) 52, a right ventricular ring terminal (V_R RING) 54, a right ventricular shocking terminal (R_V COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. In accordance with this embodiment of the present invention, the data acquisition system 90 is coupled to the right atrial lead 20, and the right ventricular lead 30 through a switching and signal conditioning circuit 98 of the switch 74 to sample cardiac signals with any one or more of the electrodes of the right atrial lead 20 and right ventricular lead 30. The circuit 98 will be described more fully herein with reference to FIG. 3.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store data from the acquisition system 90, which data may then be used for subsequent analysis by an attending physician.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In accordance with this embodiment of the present invention, the communication link 104 is further utilized for conveying the IEGMs, either prestored or in real time to the external programmer 102 for display. The IEGMs may be processed by the device 10 in a manner to be described subsequently to provide an IEGM display having the appearance of a surface EKG. Alternatively, conventional IEGM signals may be conveyed to the programmer 102 for processing, as also will be described subsequently, to provide an IEGM display having the appearance of a surface EKG.

The stimulation device 10 may further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.514 10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 540 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
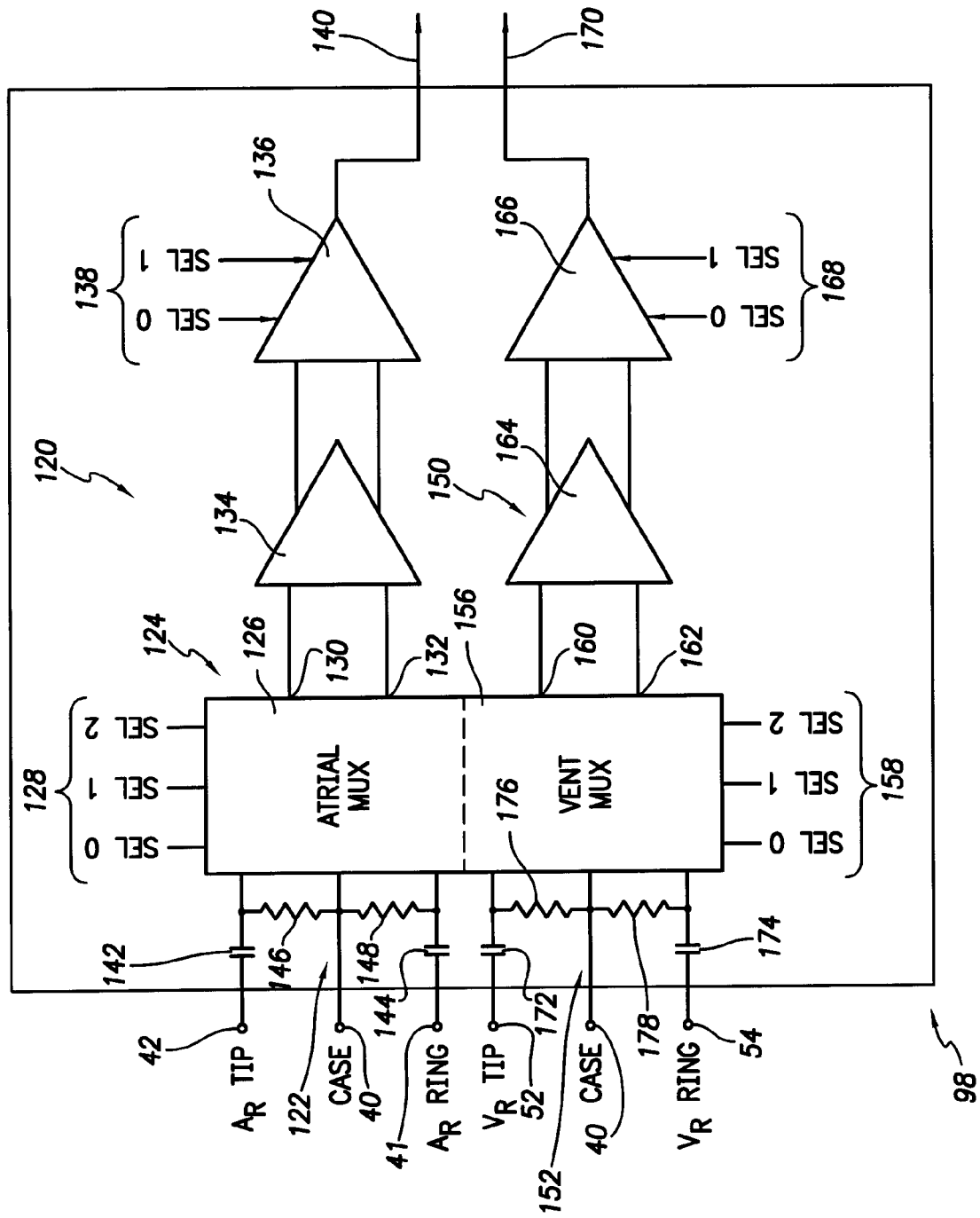
FIG. 3 is a schematic diagram of a circuit which provides high pass filtering of IEGMs within the device of FIGS. 1 and 2 to provide heart activity signals or IEGMs to be processed or to provide at least one heart activity signal for display which resembles a surface EKG in accordance with the present invention.

Referring now to FIG. 3, it illustrates a schematic circuit diagram of the switching and signal conditioning circuit 98 of FIG. 2. The circuit 98 provides an atrial based IEGM channel 120 and a ventricular based IEGM channel 150. The channel 120 includes a high pass filter 122 and the channel 150 includes a high pass filter 152. The inputs of the high pass filter 122 are coupled to the right atrial tip terminal 42, the right atrial ring terminal 41 and the case terminal 40. In a similar manner, the inputs of the high pass filter 152 is coupled to the right ventricular tip terminal 52, the right ventricular ring terminal 54, and the case terminal 40.

The outputs of the high pass filter 122 are coupled to atrial section 126 of a multiplexer 124 and the outputs of the high pass filter 152 are coupled to the ventricular section 156 of the multiplexer 124.

A first group 128 of select lines enable the selected coupling of any of the filter output combinations to the outputs 130 and 132 of the multiplexer section 126 which make inputs to an atrial channel preamplifier 134. The various switch selection combinations are illustrated in FIG. 4. For example, if all select lines (Sel 0, Sel 1, Sel 2) of group 128 are made logical zeros, a filtered IEGM signal sensed from the right atrial tip electrode 22 to the right ventricular ring electrode 34 will be provided at the outputs 130 and 132 of the multiplexer section 126 for input into the amplifier 134. The other possible electrode configurations are shown in FIG. 4 to provide an IEGM signal from the right atrial tip electrode 22 to the case 40, the right atrial tip electrode 22 to the right ventricular ring electrode 34, the right atrial tip electrode 22 to the right atrial ring electrode 21, the right atrial ring electrode 21 to the right ventricular ring electrode 34, the right atrial ring electrode 21 to the case 40, the right atrial ring electrode 21 to the right ventricular tip electrode 32, and the right atrial ring electrode 21 to the right atrial ring electrode 21. Any one of the foregoing sensing electrode configurations may be utilized for providing an atrial based IEGM signal which, when displayed, will have an appearance of a surface EKG in accordance with the present invention.

Similarly, a second group 158 of select lines enable the selected coupling of any of the filter output combinations to the outputs 160 and 162 of the multiplexer section 156 which make inputs to a ventricular channel preamplifier 164. The various switch selection combinations are illustrated in FIG. 5. For example, if all select lines (Sel 0, Sel 1, Sel 2) of group 158 are made logical zeros, a filtered IEGM signal sensed from the right ventricular tip electrode 32 to the right atrial ring electrode 21 will be provided at the outputs 160 and 162 of the multiplexer section 156 for input into the amplifier 164. The other possible electrode configurations are shown in FIG. 5 to provide a ventricular based IEGM signal from the right ventricular tip electrode 32 to the case 40, the right ventricular tip electrode 32 to the right atrial ring electrode 21, the right ventricular tip electrode 32 to the right ventricular ring electrode 34, the right ventricular ring electrode 34 to the right atrial ring electrode 21, the right ventricular ring electrode 34 to the case 40, the right ventricular ring electrode 34 to the right atrial tip electrode 22, and the right ventricular ring electrode 34 to the right ventricular ring electrode 34. Any one of the foregoing sensing electrode configurations may be utilized to provide a ventricular based IEGM signal which, when displayed, has the appearance of a surface EKG in accordance with the present invention. As may also be appreciated by those skilled in the art, a still further sensing electrode configuration could include the right ventricular coil electrode 36.

The preamplifiers 134 and 164 preferably provide the IEGMs with a high frequency cutoff or roll-off of about 250 Hz as is conventional and make input to amplifiers 136 and 166 respectively. Each of the amplifiers is a dual to single ended amplifier with programmable gain by way of select lines 138 and 168 respectively. Such amplifiers are well known in the art. The outputs 140 and 170 respectively of amplifiers 136 and 166 and then coupled to the inputs of the analog to digital acquisition system 90 of FIG. 2 which has a multiplexed output 91 to provide alternate digitized data streams of the atrial and ventricular based filtered IEGMs.

Figure 9:
FIG. 9 is a graph illustrating the frequency characteristics of a processed IEGM which, when displayed, resembles a surface EKG in accordance with the present invention.

If the sensed IEGMs are to be processed within the implanted device to provide one or both IEGMs having an appearance of a surface EKG, the component values of the high pass filters 122 and 152 are selected to provide a low frequency cutoff or roll-on no greater than 0.4 Hz while the preamplifiers 134 and 136 establish a high frequency cutoff or roll-off of no less than 20 Hz. As will be noted in FIG. 3, the high pass filter 122 includes capacitors 142 and 144 and resistors 146 and 148. Similarly, the high pass filter 152 includes capacitors 172 and 174 and resistors 176 and 178. By providing the capacitors 142, 144, 172, and 174 with a value of 0.66 microfarads and resistors 146, 148, 176 and 178 with a value of 5 megaohms, the IEGMs will be filtered with a roll-on frequency of about 0.05 Hz and a roll-off frequency of about 250 Hz provided by the IEGM preamps 134 and 164 to provide IEGMs having the appearance of a surface EKG. The frequency characteristics thus obtained are illustrated in FIG. 9. Of course, as one of ordinary skill would appreciate, the foregoing set of component values is only one example of the many different combinations of component values which may be used in practicing the present invention. Alternatively, these resistance and capacitance values could be made programmable using switchable component networks or synthesized using active circuitry.

On the other hand, if the IEGM signals are to be processed within the external programmer or display, the capacitors 142, 144, 172, and 174 and resistors 146, 148, 176, and 178 may have more conventional values. Here, for example, the resistors 146, 148, 176, and 178 may again have values of 5 megaohms and the capacitors 142, 144, 172, and 174 may have values of 0.033 microfarads. These component values together with the conventional cutoff frequencies provided by amplifiers 134 and 164 provide more conventional filtering as may be seen in the filter characteristic illustrated in FIG. 7. Here, the roll-on frequency is on the order of 1 to 2 Hz and the roll-off frequency is on the order of 250 Hz. The more conventional IEGMs to be processed by the programmer or external display in accordance with the present invention may be processed by a programmer or external display as generally illustrated in FIG. 6.

Figure 6:
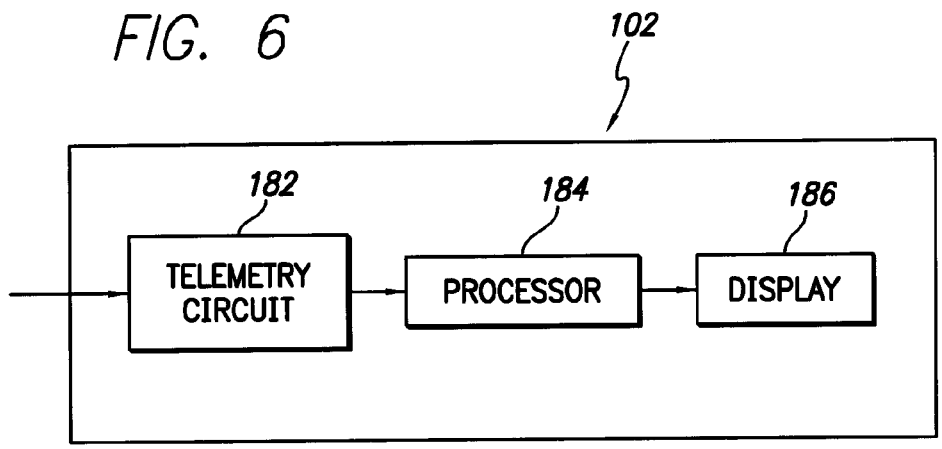
FIG. 6 is a simplified block diagram of the elements required in an external programmer for processing an IEGM and displaying the processed IEGM resembling a surface EKG.

The external programmer 102 of FIG. 6 includes a telemetry circuit 182, a processor 184, and a display 186. The telemetry circuit receives the IEGM data from the implanted device 10. The processor processes the received IEGMs by implementing a digital equalizing filter which may comprise two stages as will be described hereinafter with respect to FIG. 8. Once processed, the filtered IEGMs may be displayed on display 186 with an appearance of surface EKGs. Although not illustrated in FIG. 6, a printer may further be coupled to the processor 184 for making a hard copy of the filtered IEGMs in a conventional manner.

Figure 8:
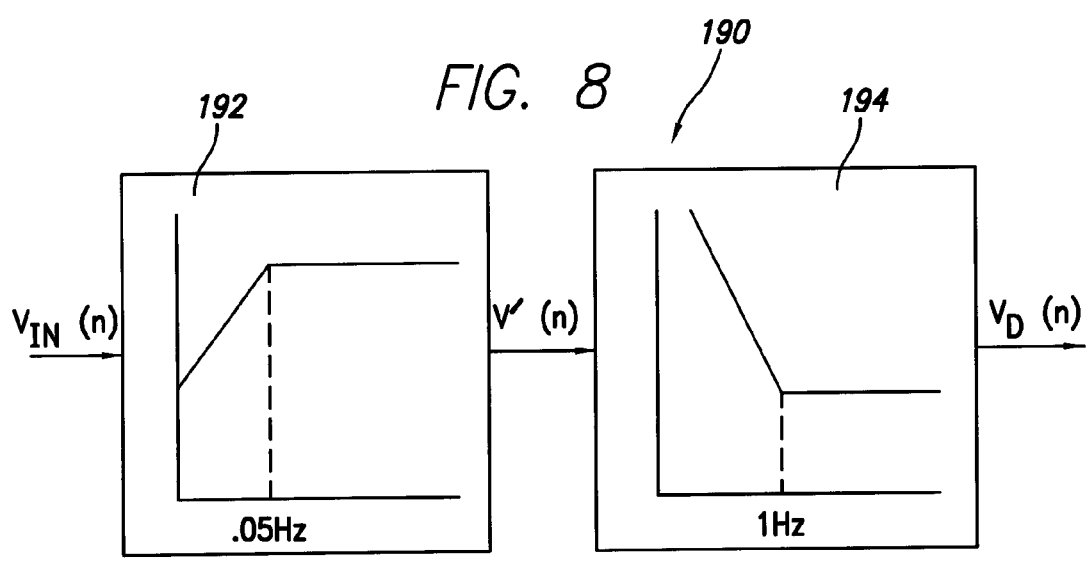
FIG. 8 is a block diagram illustrating the filtering stages of a digital filter which may be implemented by the processor of FIG. 6 in accordance with an embodiment of the present invention.

FIG. 8 shows the digital filter characteristics implemented by the processor 184 to filter the conventional IEGMs for providing IEGMs, which when displayed, have the appearance of surface EKGs. The digital filter 190 includes a first stage 192 and a second stage 194. The first stage 192 is a high pass filter with a low end cutoff of 0.05 Hz. The second stage 194 boosts the low frequencies in order to reestablish the low frequency content of the IEGMs previously lost because of the limited bandwidth available in the implanted device 10.

The first stage 192 characteristic may be represented by the equation below in a manner which may be appreciated by those skilled in the art.

Digital Filter For 0.05 Hz High Pass $$V'(n) = \frac{V'(n-1) + Vin(n) - Vin(n-1)}{\left(1 + 2\pi \frac{f_L}{f_S}\right)}$$

where $f_L$=0.05 Hz and
$f_S$=Sampling Rate=512 samples/second with the initial condition that
$V'(n-1)=V_{in}(n-1)$ furthermore $V_{in}(n)$ should be approximately a Zero mean signal to minimize settling.
n=1, 2, 3 to the final sample The second stage 194 characteristic may be represented by the equation below, also in a manner which may be appreciated by those skilled in the art.

Figure 7:
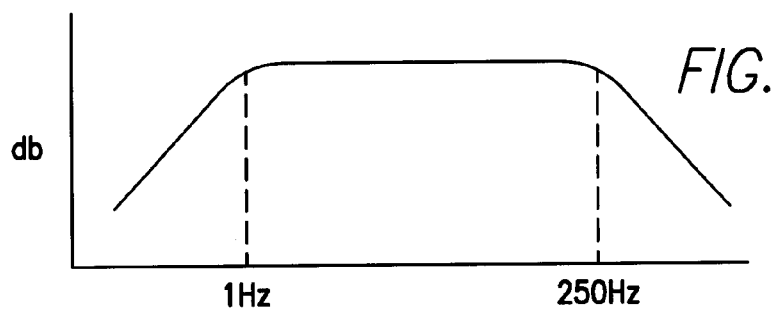
FIG. 7 is a graph illustrating the frequency characteristics of a conventional IEGM signal.

Digital Filter for Equalizer to Boost Low Frequencies $$V_o(n) = V_o(n-1) - V'(n-1) + \left(1 + 2\pi \frac{feq}{f_S}\right)V'(n)$$

where feq=1 Hz and
$f_S$=Sampling Rate=512 samples/second with the initial condition that
$V_o(n-1)=V_o'(n-1)$
n=1, 2, 3 to the final sample
After the filter 190 implemented by the processor 184 acts upon the IEGM data received from the implanted device and having the frequency characteristics shown in FIG. 7, the filtered IEGMs to be displayed will have frequency characteristics as shown in FIG. 9. Here it may be observed that the filtered IEGMs will have a low frequency roll-on of 0.05 Hz and a high frequency roll-off of about 250 Hz. The displayed IEGMs will then have the appearance of a surface EKG.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac stimulation system comprising an implantable cardiac stimulation device and an external display device, the system providing a heart activity signal of a heart for display having the appearance of a surface electrocardiogram, the system comprising:
    at least one implantable electrode that senses cardiac electrical activity and provides an intracardiac electrogram signal; and
    a filter that filters the intracardiac electrogram signal with a low frequency cutoff of no greater than about 0.4 Hz and a high frequency cutoff of no less than about 20 Hz to provide the heart activity signal for display;
    wherein the external display device comprises the filter.

2. The system of claim 1 wherein the implantable cardiac stimulation device comprises a telemetry circuit that transmits the heart activity signal to the external display device for display of the heart activity signal.

3. The system of claim 2 wherein the implantable cardiac stimulation device comprises a memory that stores the heart activity signal prior to transmission of the heart activity signal.

4. The system of claim 1 wherein the external display device comprises a memory that stores the heart activity signal prior to displaying the heart activity signal.

5. The system of claim 1 wherein the implantable cardiac stimulation device comprises a telemetry circuit that transmits the intracardiac electrogram signal to the external display device for filtering and display and wherein the external device comprises a receiving circuit that receives the intracardiac electrogram signal from the implantable cardiac stimulation device.

6. The system of claim 5 wherein the implantable cardiac stimulation device comprises a memory that stores the intracardiac electrogram signal prior to transmitting the intracardiac electrogram signal to the external display device.

7. The system of claim 5 wherein the external display device comprises a memory that stores the intracardiac signal prior to filtering and display.

8. The system of claim 1 wherein the filter is a high pass filter.

9. The system of claim 1 wherein the filter is a digital filter.

10. The system of claim 9 wherein the digital filter is an equalizer.

11. The system of claim 1 wherein the at least one electrode is adapted for implant in or proximal to an atrium of the heart.

12. The system of claim 1 wherein the at least one electrode is adapted for implant in the right atrium of the heart.

13. The system of claim 1 wherein the at least one electrode is adapted for implant in or proximal to a ventricle of the heart.

14. The system of claim 1 wherein the at least one electrode is adapted for implant in the right ventricle of the heart.

15. The system of claim 14 wherein the implantable cardiac stimulation device comprises a ventricular defibrillator and wherein the at least one electrode is a right ventricular defibrillation electrode.

16. The system of claim 1 wherein the at least one electrode comprises a first electrode adapted for implant in or proximal to an atrium of the heart and a second electrode adapted for implant in or proximal to a ventricle of the heart.

17. The system of claim 1 wherein the at least one electrode comprises a first electrode adapted for implant in the right atrium of the heart and a second electrode adapted for implant in the right ventricle of the heart.

18. In an implantable cardiac stimulation system comprising an implantable cardiac stimulation device and an external display device the system providing a heart activity signal of a heart for display having the appearance of a surface electrocardiogram, the system comprising:
    sensing means for sensing cardiac electrical activity and providing an intracardiac electrogram signal; and
    filter means for filtering the intracardiac signal with a low frequency cutoff of no greater than 0.4 Hz and a high frequency cutoff of no less than 20 Hz for providing the heart activity signal for display;
    wherein the external device comprises the filter means.

19. The system of claim 18 wherein the implantable cardiac stimulation device comprises telemetry means for transmitting the heart activity signal to the external device for display of the heart activity signal.

20. The system of claim 19 wherein the implantable cardiac stimulation device comprises memory means for storing the heart activity signal prior to transmission of the heart activity signal.

21. The system of claim 20 wherein the external device comprises memory means for storing the heart activity signal prior to displaying the heart activity signal.

22. The system of claim 18 wherein the implantable cardiac stimulation device comprises telemetry means for transmitting the intracardiac electrogram signal to the external device for filtering and display and wherein the external device comprises receiving means for receiving the intracardiac electrogram signal from the implantable cardiac stimulation device.

23. The system of claim 22 wherein the implantable cardiac stimulation device comprises memory means for storing the intracardiac electrogram signal prior to transmitting the intracardiac electrogram signal to the external device.

24. The system of claim 22 wherein the external device comprises memory means for storing the intracardiac signal prior to filtering and display.

25. The system of claim 18 wherein the filter means comprises a high pass filter.

26. The system of claim 18 wherein the filter means comprises a digital filter.

27. The system of claim 26 wherein the digital filter is an equalizer.

28. The system of claim 18 wherein the sensing means comprises at least one electrode adapted for implant in or proximal to an atrium of the heart.

29. The system of claim 18 wherein the sensing means comprises at least one electrode adapted for implant in the right atrium of the heart.

30. The system of claim 18 wherein the sensing means comprises at least one electrode adapted for implant in or proximal to a ventricle of the heart.

31. The system of claim 18 wherein the sensing means comprises at least one electrode adapted for implant in the right ventricle of the heart.

32. The system of claim 31 wherein the implantable cardiac stimulation device comprises a ventricular defibrillator and wherein the sensing means comprises at least a right ventricular defibrillation electrode.

33. The system of claim 18 wherein the sensing means comprises a first electrode adapted for implant in or proximal to an atrium of the heart and a second electrode adapted for implant in or proximal to a ventricle of the heart.

34. The system of claim 18 wherein the sensing means comprises a first electrode adapted for implant in the right atrium of the heart and a second electrode adapted for implant in the right ventricle of the heart.

35. In an implantable cardiac stimulation system comprising an implantable cardiac stimulation device and an external display device, a method of providing a heart activity signal of a heart which, when displayed, resembles a surface electrocardiogram, the method comprising:

sensing cardiac electrical activity with at least one implanted electrode to provide an intracardiac electrogram signal; and filtering the intracardiac signal with a high pass filter having a low frequency cutoff of no greater than 1 to 2 Hz and a high frequency cutoff of no less than 20 Hz;

transmitting the filtered intracardiac signal to the external display device;

further filtering the filtered intracardiac signal with an equalizing filter to resemble a surface electrocardiogram, the further filtering step performed within the external display device.

36. The method of claim 35 comprising the further step of storing the heart activity signal in a memory prior to transmitting heart activity signal to the external display device.

37. The method of claim 36 comprising the further step of storing the heart activity signal within the external display device prior to displaying the heart activity signal.

38. The method of claim 35 wherein the equalizing filter is a digital equalizing filter having a first stage to high pass filter with a low end cutoff of about 0.05 Hz and a second stage to boost low frequencies.

39. An implantable cardiac stimulation system comprising:

an implantable cardiac stimulation device to provide a heart activity signal of a heart;

an implantable electrode coupled to the implantable cardiac stimulating device, the implantable electrode to sense cardiac electrical activity and to provide an intracardiac electrogram signal; and a filter to filter the intracardiac electrogram signal with a low frequency cutoff of no greater than about 0.4 Hz and a high frequency cutoff of no less than about 20 Hz to provide a filtered intracardiac electrogram signal, the filtered intracardiac electrogram signal resembling a surface electrocardiogram; and an external display device to display the filtered intracardiac electrogram signal.

40. An implantable cardiac stimulation system comprising:

an implantable cardiac stimulation device to provide a heart activity signal of a heart;

an implantable electrode coupled to the implantable cardiac stimulating device, the implantable electrode to sense cardiac electrical activity and to provide an intracardiac electrogram signal;

a first filter to filter the intracardiac electrogram signal with a low frequency cutoff of no greater than about 1 to 2 Hz and a high frequency cutoff of no less than about 250 Hz to provide a filtered intracardiac electrogram signal, and an external display device having a second filter to further filter the filtered intracardiac electrogram signal, the further filtered intracardiac electrogram resembling a surface electrocardiogram, and the external display device to display the further filtered intracardiac electrogram signal.

41. The system of claim 40 wherein the second filter is a digital equalizing filter.

42. The system of claim 41 wherein the digital equalizing filter has a and a second stage.

43. The system of claim 42 wherein the first stage is a high pass filter end cutoff of about 0.05 Hz and the second stage boosts low frequencies.

* * * * *